US012765813B2

(12) United States Patent
Fuerst et al.

(10) Patent No.: US 12,765,813 B2
(45) Date of Patent: Oct. 20, 2026

(54) METHOD FOR DETERMINING AN ANALYTE CONCENTRATION IN A FLUID

(71) Applicant: Roche Diabetes Care, Inc., Indianapolis, IN (US)

(72) Inventors: Angelika Fuerst, Mannheim (DE); Gernot Hochmuth, Mannheim (DE); Kirill Sliozberg, Mannheim (DE); Alexander Steck, Hirschberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 740 days.

(21) Appl. No.: 18/153,828

(22) Filed: Jan. 12, 2023

(65) Prior Publication Data

US 2023/0148919 A1 May 18, 2023

Related U.S. Application Data

(63) Continuation of application No. PCT/EP2021/069293, filed on Jul. 12, 2021.

(30) Foreign Application Priority Data

Jul. 13, 2020 (EP) .................................... 20185452

(51) Int. Cl.

| | |
|---|---|
| ***A61B 5/1473*** | (2006.01) |
| ***A61B 5/00*** | (2006.01) |
| ***A61B 5/145*** | (2006.01) |

(52) U.S. Cl.

CPC ........ *A61B 5/1473* (2013.01); *A61B 5/14532* (2013.01); *A61B 5/7264* (2013.01)

(58) Field of Classification Search

CPC . A61B 5/1473; A61B 5/14532; A61B 5/7264; A61B 5/14503; G01N 33/5438; G01N 33/66

See application file for complete search history.

(56) References Cited

U.S. PATENT DOCUMENTS

| | | | |
|---|---|---|---|
| 10,088,476 | B2 | 10/2018 | Braun et al. |
| 2004/0108226 | A1 | 6/2004 | Polychronakos et al. |

(Continued)

FOREIGN PATENT DOCUMENTS

| | | | |
|---|---|---|---|
| WO | WO 2019/115687 | A1 | 6/2019 |

OTHER PUBLICATIONS

International Search Report and Written Opinion of the International Searching Authority, PCT/EP2021/069293, Sep. 1, 2021, 10 pages.

(Continued)

*Primary Examiner* — Samuel P Siefke

(74) *Attorney, Agent, or Firm* — Bose McKinney & Evans LLP

(57) ABSTRACT

A method for determining an analyte concentration in a fluid using an analyte sensor having at least two measurement electrodes is disclosed. One of the measurement electrodes has an analyte-responsive polymer gel. The method includes contacting at least the analyte-responsive polymer gel with the fluid having the analyte, generating a non-continuous fast-transient voltage signal and applying the non-continuous fast-transient voltage signal to the measurement electrodes, measuring a response signal, and evaluating the response signal to determine the analyte concentration.

13 Claims, 6 Drawing Sheets

(56) References Cited

U.S. PATENT DOCUMENTS

| | | | |
|---|---|---|---|
| 2015/0283247 A1* | 10/2015 | Auzely-Velty ...... C08B 37/0072 514/777 |
| 2017/0119289 A1 | 5/2017 | Yoshioka et al. |
| 2017/0181669 A1 | 6/2017 | Lin et al. |
| 2019/0227028 A1 | 7/2019 | Patolsky et al. |

OTHER PUBLICATIONS

Webber et al., Smart Approaches to Glucose-Responsive Drug Delivery, J Drug Target, 2015, vol. 23, Nos. 7-8, pp. 651-655.

Matsumoto et al., Glucose-responsive polymer gel bearing phenylborate derivative as a glucose-sensing moiety operating at the physiological pH, Biomacromolecules, 2004, vol. 5, No. 3, pp. 1038-1045.

* cited by examiner

| | |
|---|---|
| Equation | y=a+b*x |
| Plot | Normalized impedance |
| Weight | No Weighting |
| intercept | 1.76289 ± 0.46442 |
| Slope | 0.15655 ± 0.0016 |
| Residual Sum of Squares | 197.85399 |
| Pearson´s r | 0.99757 |
| R-Square (COD) | 0.99514 |
| Adj. R-Square | 0.99504 |

METHOD FOR DETERMINING AN ANALYTE CONCENTRATION IN A FLUID

RELATED APPLICATIONS

This application is a continuation of PCT/EP2021/069293, filed Jul. 12, 2021, which claims priority to EP 20 185 452.8, filed Jul. 13, 2020, both of which are hereby incorporated herein by reference.

BACKGROUND

This disclosure discloses a method for determining an analyte concentration in a fluid using an analyte sensor, and an analytical system. The analyte sensor may be or may comprise a sensor configured for measuring conductivity. In one embodiment, the analyte sensor may be configured for insertion into a body tissue of a user, specifically an insertable or implantable sensor for monitoring of the at least one analyte in the body tissue and/or in a body fluid within the body tissue. The method and devices according to this disclosure may be used for detecting at least one analyte present in a fluid such as in the body fluid, in particular the method and devices are applied in the field of detecting one or more analytes such as glucose, lactate, triglycerides, cholesterol or other analytes, preferably metabolites, in body fluids such as blood or interstitial fluid or other body fluids, both in the field of professional diagnostics, in the field of hospital point of care, in the field of personal care and in the field of home monitoring. However, other fields of application are feasible.

In the field of medical technology and diagnostics, a large number of devices and methods for detecting at least one analyte in a fluid are known. For example, the methods and devices may be used for detecting at least one analyte present in one or both of a body tissue or a body fluid, in particular one or more analytes such as glucose, lactate, triglycerides, cholesterol or other analytes, preferably metabolites, in body fluids such as blood or interstitial fluid or other body fluids. Without restricting the scope of this disclosure, in the following, mainly reference is made to the determination of glucose by an analyte sensor as an exemplary and preferred analyte.

Methods and techniques are generally known for determining an analyte concentration in a body fluid using sensor materials which change their dimension while in contact with an analyte solution. For example, U.S. Pat. No. 10,088,476 B2 describes hydrogel and organogel sensors as well as their application to continuous analyte monitoring. The sensor can include a hydrogel or organogel matrix. Standard and inverse designs are provided. In one embodiment, the matrix can include a molecular recognition agent for an analyte, and a volume resetting agent that reversibly binds with the molecular recognition agent. Reversible crosslinks between the molecular recognition agent and volume resetting agent can change the volume of the matrix upon interacting with the analyte via a competitive binding process.

U.S. Publication No. 2004/0108226 A1 describes a device and method for glucose quantification in a liquid medium using a reference electrode, a counter electrode and a working electrode with a semipermeable membrane. A reversible binding of glucose to Concanavalin A and its measurement using impedance measurement is described.

U.S. Publication No. 2019/227028 A1 describes a sensing system and a method utilizing the same for determining and/or monitoring a presence and/or level of an analyte in a sample. The sensing system comprises a nanostructure having covalently attached thereto a hydrogel which as associated therewith a sensing moiety which selectively interacts with the analyte. The sensing moiety comprises an enzyme. Upon contacting the analyte, the nanostructure exhibits a detectable change in an electrical property.

U.S. Publication No. 2017/181669 A1 discloses a receptor which is capable of binding to a target analyte. The receptor can be used in a microdevice for determining and/or monitoring an analyte in a body fluid or sample. Differential measurements using the microdevice allow determination of the target analyte concentration.

U.S. Publication No. 2017/119289 A1 describes a sweat collection device which includes a collection section and a discharge section. The sweat collection device includes a gel-like response section which responds to lactic acid contained in sweat.

However, despite these achievements, there is still a need for improving determination of an analyte concentration, in particular for reducing complexity of the determination of the analyte concentration and costs reduction of measurement electronics while allowing determination of the analyte concentration with high precision.

SUMMARY

It is therefore an objective of this disclosure to provide a method for determining an analyte concentration in a fluid using an analyte sensor and an analytical system, which at least partially avoid the shortcomings of known devices and methods of this kind and which at least partially address the above-mentioned challenges. Specifically, a method and analytical system for determining an analyte concentration shall be provided which allow for a precise determination of an analyte concentration using simple and therefore cost-efficient measurement electronics.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "analyte-responsive polymer gel," "measurement electrode," and "response signal," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a method for determining an analyte concentration in a fluid using an analyte sensor is disclosed.

The term "analyte" as used herein is a broad term and is to be given its ordinary and customary meaning to a person of ordinary skill in the art and is not to be limited to a special or customized meaning. The term specifically may refer, without limitation, to an arbitrary element, component or compound which may be present in a fluid, specifically in a body fluid, and the concentration of which may be of interest for a user. Specifically, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Specifically, the analyte may be glucose. Additionally or alternatively, however, other types of analytes may be determined and/or any combination of analytes may be determined.

The term "fluid" as used herein is a broad term and is to be given its ordinary and customary meaning to a person of ordinary skill in the art and is not to be limited to a special or customized meaning. The term specifically may refer, without limitation, to all fluids of interest known to comprise or suspected to comprise the analyte. The fluid may be an electrolyte of a galvanic cell as will be described in more detail below. Specifically, the fluid may be a body fluid. The term "body fluid" as used herein is a broad term and is to be given its ordinary and customary meaning to a person of ordinary skill in the art and is not to be limited to a special or customized meaning. The term specifically may refer, without limitation, to all body fluids of a user known to comprise or suspected to comprise the analyte of this disclosure, including interstitial fluid, blood, plasma, lacrimal fluid, urine, lymph, cerebrospinal fluid, bile, stool, sweat, and saliva. Generally, an arbitrary type of body fluid may be used. Preferably, the body fluid is a body fluid which is present in a body tissue of a user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo. However, other non-in vivo applications are possible.

The term "determining a concentration of at least one analyte" as used herein is a broad term and is to be given its ordinary and customary meaning to a person of ordinary skill in the art and is not to be limited to a special or customized meaning. The term specifically may refer, without limitation, to a quantitative detection of the at least one analyte. As a result of the determination, at least one signal, such as at least one measurement signal, and/or at least one measurement value may be produced and/or provided which characterizes an outcome of the determination. The signal specifically may be or may comprise at least one electronic signal such as at least one voltage and/or at least one current. The at least one signal may be or may comprise at least one analogue signal and/or may be or may comprise at least one digital signal.

The term "sensor" as used herein is a broad term and is to be given its ordinary and customary meaning to a person of ordinary skill in the art and is not to be limited to a special or customized meaning. The term specifically may refer, without limitation, to an arbitrary element or device configured for detecting at least one condition or for measuring at least one measurement variable. The term "analyte sensor" as used herein is a broad term and is to be given its ordinary and customary meaning to a person of ordinary skill in the art and is not to be limited to a special or customized meaning. The term specifically may refer, without limitation, to a sensor configured for detecting quantitatively or qualitative at least one analyte. As outlined above, the analyte sensor may be used for in vivo or in vitro measurements. The analyte sensor may be configured for being used for a plurality different applications such as for monitoring an analyte in a body fluid or for monitoring at least one fermentation process. Even other applications are possible.

The analyte sensor comprises at least two measurement electrodes. The term "electrode" as used herein is a broad term and is to be given its ordinary and customary meaning to a person of ordinary skill in the art and is not to be limited to a special or customized meaning. The term specifically may refer, without limitation, to an, generally arbitrary shaped, electrical conductor. The term "measurement electrode" as used herein is a broad term and is to be given its ordinary and customary meaning to a person of ordinary skill in the art and is not to be limited to a special or customized meaning. The term specifically may refer, without limitation, to an electrode which is or can be brought in contact with a fluid such as an electrolyte, in particular with a body fluid. The analyte sensor may be a two electrode sensor. However, embodiments are possible in which the analyte sensor comprises more than two electrodes.

At least one of the measurement electrodes comprises an analyte-responsive polymer gel. Embodiments are possible, wherein both measurement electrodes comprise an analyte-responsive polymer gel. Preferably, the analyte sensor comprises one measurement electrode which comprises the analyte-responsive polymer gel, whereas a second measurement electrode does not comprise the analyte-responsive polymer gel. The measurement electrode comprising the analyte-responsive polymer gel is also referred to as working electrode. The measurement electrode which does not comprise any analyte-responsive polymer gel is typically referred to as counter electrode, reference electrode or combined counter/reference electrode. This measurement electrode setup as such is generally known to the skilled person.

The term "polymer gel" as used herein is a broad term and is to be given its ordinary and customary meaning to a person of ordinary skill in the art and is not to be limited to a special or customized meaning. The term specifically may refer, without limitation, to a solid material comprising a three-dimensional polymeric matrix or network in the medium of a liquid. The term "analyte-responsive" polymer gel as used herein is a broad term and is to be given its ordinary and customary meaning to a person of ordinary skill in the art and is not to be limited to a special or customized meaning. The term specifically may refer, without limitation, to a feature of the polymer gel of changing at least one property, such as overall charge and/or volume, depending on presence of the analyte. For example, the analyte may be glucose and the analyte-responsive polymer gel may be a glucose-responsive polymer gel.

For example, the analyte-responsive polymer gel may comprise a phenylborate. For example, the analyte-responsive polymer gel may comprise 3-(Acrylamido)phenylboronicacid, 4-Vinylpyridine and Divinylbenzene or Acrylamide and 3-acrylamidophenylboronic acid or ethyl acrylate, 3-(Acrylamido)phenylboronic acid, N-vinylpyrrolidone and ethylene glycol dimethacrylate. Analyte-responsive polymer gels may generally comprise boronic acid groups and/or concanavalin A groups (Matthew J. Webber, 2015 doi: 10.3109/1061186X.2015.1055749).

For example, the analyte-responsive polymer gel may comprise poly(N-isopropylacryl-amide). Analyte-responsive polymer gels are generally known. For example, glucose-responsive polymer gels are described in "Glucose-Responsive Polymer Gel Bearing Phenylborate Derivative as a Glucose-Sensing Moiety Operating at the Physiological pH," Matsumoto et al., Biomacromolecules 2004, 5, 1038-1045, incorporated herein by reference. Without being bound by theory, phenylboronic acid and its derivatives are known to form reversible covalent complexes with diol units, such as with glucose. Phenylboronic acid compounds in water exist in equilibrium between the uncharged and the charged forms. Only the charged form can make a relatively stable complex with glucose through a reversible covalent bonding, whereas the complex between the uncharged form and glucose is unstable in water due to its high susceptibility to hydrolysis. Because the complex between the charged phenylborate and glucose itself is also anionically charged, the further addition of glucose induces a shift in the equilibrium to the direction of increasing the fraction of the charged forms, and vice versa. Therefore, the introduction of the phenylborate group into an amphiphilic polymer gel structure, such as that of poly(N-isopropylacryl-amide) (PNIPAAm) gel, brings about a reversible volume transition of the gel, which is mainly due to the change in the counterions' osmotic pressure synchronized with the change in the glucose concentration. The analyte-responsive polymer gel may be configured for changing volume and/or charge, in particular continuously, in the presence of glucose. The change in the overall gel charge and volume may lead to the change of the analyte-responsive polymer gels' ionic conductivity, which can be measured as will be described in more detail below. For example, the analyte sensor may be a glucose sensor comprising boronic acid based glucose-responsive polymer gel. As will be described in detail below, the concentration of glucose can be determined using a fast-transient voltage signal for the measurement of the analyte sensor conductivity, which is related to the glucose concentration.

For example, in an embodiment the analyte-responsive polymer gel may have the following composition:

| | | |
|---|---|---|
| 3APBA | 3-(Acrylamido)phenylboronic acid | 5 mol % |
| 4VP | 4-Vinylpyridine | 93 mol % |
| DVB | Divinylbenzene | 1 mol % |
| | Irgacure 2959 | 1 mol % |

Irgacure 2959 is also known as $\alpha$-Hydroxy-4-(2-hydroxyethoxy)-$\alpha$-methylpropiophenon.

It is clear to the skilled person that the above-described composition of the analyte responsive polymer gel corresponds to the starting materials for the analyte responsive polymer gel. In the analyte-responsive polymer gel, the compounds are comprised in their reacted form. This is clear to the skilled person and known as such.

In one embodiment of the analyte sensor, the analyte sensor may comprise at least one isolating substrate. The isolating substrate may comprise a convenient thickness. The isolating substrate may comprise one or more of plastic, such as polyethylene terephthalate (PET), polyimide, polyvinyl chloride (PVC) or the like, ceramics, metallic substrate coated by any insulating layer, such as photoresist layer. The isolating substrate may be coated by a conductive layer, for instance gold, carbon, palladium, but also any other inert conductive material, also organic conductors, like doped polythiophene. Also doped metal oxides, like ITO (indium tin oxide) or FTO (fluorine-doped tin oxide) may be used as suitable conductors. Depending on the conductive layer used, suitable structuring method may be chosen to create the measurement electrodes, having preferentially an interdigitated structure. For example, a gold layer may be used. The structuring can be done using laser ablation or chemical etching, but also any other suitable processing. Also sputtering, in particular of gold, using lift-off structuring can be used. After structuring at least one of the measurement electrodes may be coated by, e.g., photoresist such as to leave only the interdigitated structure exposed with well-defined surface area of the two measurement electrodes. Exposed portions of at least one of the measurement electrodes may be coated by the analyte-responsive polymer gel using, e.g., slot-die coating or simple dip-coating.

In one embodiment of the analyte sensor, the analyte sensor may be manufactured using a thin foil, e.g., 100 μm, double side coated with a conductive material, e.g., sputtered gold, screen-printed carbon, or anything else. The foil may be cut at the way, to obtain an "I"-shaped sensor. One end of the I-shaped sensor may be used for contacting to corresponding measurement electronics and the other end may be used as analyte sensitive portion of the analyte sensor comprising the analyte-responsive polymer gel. In order to convert the end into an analyte sensitive portion, the analyte sensor may be dip-coated in a solution of the glucose responsive polymer gel. For example, a layer thickness may be from 6 to 30 μm, preferentially the layer thickness may be 8 μm. Viscosity of the solution, dipping parameters, such as speed, temperature and others may be controlled at the way to obtain a glucose responsive polymer gel layer of suitable thickness. Preferentially, a non-coated portion of the conductive material is coated by an insulating layer.

The method comprises the method steps as given in the corresponding independent claim and as listed as follows. The method steps may be performed in the given order. Further, one or more of the method steps may be performed in parallel and/or in a time overlapping fashion. Further, one or more of the method steps may be performed repeatedly. Further, additional method steps may be present which are not listed.

The method comprises the following steps:

a) contacting at least the analyte-responsive polymer gel of the analyte sensor with the fluid comprising the analyte;
b) generating at least one fast-transient voltage signal and applying the fast-transient voltage signal to the measurement electrodes;
c) measuring at least one response signal;
d) determining the analyte concentration by evaluating the response signal.

The term “contacting” as used herein is a broad term and is to be given its ordinary and customary meaning to a person of ordinary skill in the art and is not to be limited to a special or customized meaning. The term specifically may refer, without limitation, to a process of exposing the at least one measurement electrode comprising the analyte-responsive polymer gel to the fluid. The analyte sensor may be an in-vivo sensor. The term “in-vivo sensor” as used herein is a broad term and is to be given its ordinary and customary meaning to a person of ordinary skill in the art and is not to be limited to a special or customized meaning. The term specifically may refer, without limitation, to a sensor which is configured for being at least partially implanted into a body tissue of a user. The analyte sensor may be a subcutaneous analyte sensor. The analyte sensor may be configured for implantation into a body tissue of the user. More specifically the analyte sensor may be configured for continuous monitoring of the analyte. The analyte sensor may be fully implantable or partially implantable.

The term “user” as used herein is a broad term and is to be given its ordinary and customary meaning to a person of ordinary skill in the art and is not to be limited to a special or customized meaning. The term specifically may refer, without limitation, to a human being or an animal, independent from the fact that the human being or animal, respectively, may be in a healthy condition or may suffer from one or more diseases. As an example, the user may be a human being or an animal suffering from diabetes. However, additionally or alternatively, this disclosure may be applied to other types of users. The analyte sensor may be placed in vivo to carry out step a), and subsequently the further method steps.

The term “fast-transient voltage signal” as used herein is a broad term and is to be given its ordinary and customary meaning to a person of ordinary skill in the art and is not to be limited to a special or customized meaning. The term specifically may refer, without limitation, to at least one arbitrary voltage signal, in particular an arbitrary voltage change in between two electrodes. The fast-transient voltage signal may have fast transient signal flanks, in particular two very steep edges. The fast-transient voltage signal may comprise a square waveform and/or a sine wave form. Specifically, the fast-transient voltage signal may comprise a fast transition square wave.

The fast-transient voltage signal may comprise a non-continuous signal such as a pulse. The term “pulse” as used herein is a broad term and is to be given its ordinary and customary meaning to a person of ordinary skill in the art and is not to be limited to a special or customized meaning. The term specifically may refer, without limitation, to a signal having a transient change in the amplitude of the signal from a first value, also denoted baseline value, to a second value, followed by a return to the baseline value or at least approximately to the baseline value. The second value may be a higher or lower value than the baseline value. A pulse duration may be ≤50 μs, preferably ≤20 μs, more preferably ≤10 μs. The duration of the single pulse must be sufficiently long to be able to record its propagation. The fast-transient voltage signal may comprise a pulse having two edges: a leading edge or front edge, which is a first edge of the pulse and a trailing edge or back edge, which is a second edge of the pulse.

The term “fast-transient” as used herein is a broad term and is to be given its ordinary and customary meaning to a person of ordinary skill in the art and is not to be limited to a special or customized meaning. The term specifically may refer, without limitation, to time range between first and second values of the signal flank.

The terms first and second “value” may refer to regions or points of the fast-transient voltage signal, in particular its amplitude. The first value may be the baseline value. The first value may be a local and/or overall minimum of the fast-transient voltage signal. The first value may be a first plateau of the fast-transient voltage signal. The first value may refer to a time point with no voltage is applied to the measurement electrodes. The second value may be a local and/or overall extremum of the fast-transient voltage signal. The second value may be a second plateau of the fast-transient voltage signal, which may be reached during application of the fast-transient voltage signal. The second value may be extremum of the fast-transient voltage signal.

The term “signal flank” as used herein is a broad term and is to be given its ordinary and customary meaning to a person of ordinary skill in the art and is not to be limited to a special or customized meaning. The term specifically may refer, without limitation, to transition of a signal amplitude from low to high signal value or from high to low signal value. The signal flank may be a rising signal flank or a falling signal flank. The signal flank of the fast-transient voltage signal may have a change in signal from the first value of the signal flank to the second value of the signal flank in a microsecond to nanosecond range. The signal flank may also be referred to as edge. The fast-transient voltage signal may have a low-to-high transition of a signal amplitude, which is equivalent to rising or positive signal flank, or high-to-low transition of a signal amplitude, which is equivalent to falling or negative signal flank. The fast-transient voltage signal may have steep edges. Specifically, the fast transition square wave may have a change in voltage from the first value to the second value below or equal 50 ns, preferably below or equal 20 ns. The change in voltage from the first value to the second value may be even faster and may be only limited by electronics such as by a fast-transient voltage generator (DAC, DO or others) or a read-out unit (voltage amplifier, ADC, or others). The faster the change of voltage (higher slew rate) and the sharper the transition to the plateau, the more precise the analyte concentration can be determined. The duration of the single fast-transient voltage signal must be sufficiently long to record the response voltage.

The fast-transient voltage signal may be applied to the measurement electrodes with a known amplitude. The amplitude of the fast-transient voltage signal may vary in a broad range and must be optimized for a given set-up. Generally, the lower limit may be limited by the readout technique, which must record the response voltage, mostly by its input range and resolution and may require an additional sufficiently fast voltage amplifier.

The fast-transient voltage signal may be applied at least once to the measurement electrodes. The fast-transient voltage signal may be applied after a certain time after contacting the analyte sensor with the fluid. The fast-transient voltage signal may be applied repeatedly to the measurement electrodes, in particular periodically. The fast-transient voltage signal may be applied repeatedly to the measurement electrodes, in particular in time intervals from minutes to seconds. A measurement frequency may depend on how often measurement values are required. The method may further comprise determining a combined measurement value for reducing a measurement uncertainty. The determining of a combined measurement value may comprise determining of one or more of an average value, a mean value, a median, using a more complex filter such as a Kalman filter. For example, measurement values may be obtained every second and the 60 measurement results may be averaged to a minute-value. The measurement frequency may depend on the application of the analyte sensor. For monitoring of analyte in a body fluid the frequency may be short, whereas for monitoring a fermentation process such as in wine or beer the measurement frequency may be less frequent.

The fast-transient voltage signal may be generated by at least one signal generator device. The term "signal generator device" generally refers to a device, for example, a voltage source, being configured to generate a voltage signal. The "signal generator device" may also be referred to as "voltage generating device." The signal generator device may comprise at least one voltage source. The signal generator device may comprise at least one function generator selected from the group consisting of: at least one square wave generator and at least one sine wave generator. The signal generator device may also generate a single pulse which may be unsymmetrical. "Unsymmetrical" in this context means that a first pulse may be different from a second pulse and/or a third pulse and/or any other subsequent pulse. The signal generator device may be part of measurement electronics of the analyte sensor and/or may be connected to the analyte sensor and may be designed as a separate device. The signal generator device may be configured for applying the fast-transient voltage signal to the measurement electrodes.

The term "applying the fast-transient voltage signal to the measurement electrodes" as used herein is a broad term and is to be given its ordinary and customary meaning to a person of ordinary skill in the art and is not to be limited to a special or customized meaning. The term specifically may refer, without limitation, to providing the fast-transient voltage signal to one of the measurement electrodes.

The analyte sensor may be represented as an equivalent circuit. Each measurement electrode of the analyte sensor may have a capacity caused by a formed electrochemical double layer, denoted $C_{dl}$. Ionic resistivity of the analyte-responsive polymer gel, specifically a layer of polymer gel, between the two measurement electrodes may be represented as $R_{GRPC}$. Moreover, charge transfer resistances $R_{ct}$ may be present at electrode-electrolyte interfaces. At the rest there is no potential applied between the both measurement electrodes and surfaces of the measurement electrodes may be inert. In particular, there is no electron transfer between the electrodes and electrolyte and the $R_{ct}$ is, therefore, infinitely large. The two $C_{dl}$ may be connected serially and are thus not differentiable. Thus, the whole analyte sensor can be represented as a single $C_{dl}$ serially connected with $R_{GRPC}$. The signal generator device may be configured for keeping the potential difference between the two measurement electrodes at zero in the rest.

The term "response signal" as used herein is a broad term and is to be given its ordinary and customary meaning to a person of ordinary skill in the art and is not to be limited to a special or customized meaning. The term specifically may refer, without limitation, to measured propagation of the applied fast-transient voltage signal. The terms "response signal" and "propagation" are used herein as synonyms. The response signal may be a change of the applied fast-transient voltage signal. The response signal may directly or indirectly refer to equivalent series resistance of the analyte sensor. The response signal may be the ohmic and capacitive characterization of the analyte sensor in its in-vivo surroundings.

The response signal typically refers to a voltage response. In general, the response signal does not relate to a current response.

The response voltage may be measured at a reference resistance. The analyte sensor may comprise at least one reference resistance in series with an ionic resistivity of the analyte-responsive polymer gel. The reference resistance may be selected suitable for determining a value to be measured such as the electrical resistance of the ionic resistivity of the analyte-responsive polymer gel $R_{GRPC}$. A value $R_{ref}$ of the reference resistance may be preferentially in the range of the $R_{GRPC}$. The reference resistance may be an average value determined, specifically pre-determined, from a plurality of reference measurements. The reference resistance must reflect the measurement range of the analyte-responsive polymer gel. The reference resistance may reflect required measurement tolerances. During determination of the $R_{GRPC}$ determination, the signal generator device may apply the fast-transient voltage signal with known amplitude $U_1$ to the measurement electrodes. Simultaneously a voltage drop $U_2$ may be measured at the reference resistance $R_{ref}$.

Evaluating the response signal may comprises determining the equivalent series resistance of the analyte sensor. Knowing the amplitude of the applied voltage and the amplitude measured at the $R_{ref}$, as well as the value of the $R_{ref}$, $R_{GRPC}$ can be calculated as:

$$R_{GRPC} = R_{ref}\frac{U_2}{(U_1 - U_2)}$$

The evaluation of the response signal may be performed by at least one evaluation device. As used herein, the term "evaluation device" generally refers to an arbitrary device being configured to derive at least one item of information from data. The evaluation device may be configured to derive the equivalent series resistance. As an example, the evaluation device may be or may comprise one or more integrated circuits, such as one or more application-specific integrated circuits (ASICs), and/or one or more data processing devices, such as one or more computers, preferably one or more microcomputers and/or microcontrollers. Additional components may be comprised, such as one or more preprocessing devices and/or data acquisition devices, such as one or more devices for receiving and/or preprocessing of the response signal, such as one or more converters and/or one or more filters. The evaluation device may comprise one or more data storage devices. The evaluation device may comprise one or more interfaces, such as one or more wireless interfaces and/or one or more wire-bound interfaces. The evaluation device may comprise a microprocessor, a cellular phone, a smart phone, a personal digital assistant, a personal computer, and/or a computer server.

The evaluation may further comprise determining the concentration of the analyte from the equivalent series resistance by using at least one pre-determined relationship. For example, the pre-determined relationship may be a linear relationship. For example, the pre-determined relationship may be stored in at least one database of the evaluation device.

Specifically, this disclosure proposes determination of a glucose concentration in a fluid by using an analyte sensor comprising the analyte-responsive polymer gel.

This disclosure further discloses and proposes a computer program including computer-executable instructions for performing the method for determining an analyte concentration according to this disclosure in one or more of the embodiments enclosed herein, when the program is executed on a computer or computer network. Specifically, the computer program may be stored on a computer-readable data carrier. Thus, specifically, one, more than one or even all of method steps, as indicated above, may be performed by using a computer or a computer network, preferably by using a computer program.

This disclosure further discloses and proposes a computer program product having program code means, in order to perform the method for determining an analyte concentration according to this disclosure in one or more of the embodiments enclosed herein, when the program is executed on a computer or computer network. Specifically, the program code means may be stored on a computer-readable data carrier.

Further, this disclosure discloses and proposes a data carrier having a data structure stored thereon, which, after loading into a computer or computer network, such as into a working memory or main memory of the computer or computer network, may execute the method according to one or more of the embodiments disclosed herein.

This disclosure further proposes and discloses a computer program product with program code means stored on a machine-readable carrier, in order to perform the method according to this disclosure, in particular method steps b) to d), according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, this disclosure proposes and discloses a modulated data signal which contains instructions readable by a computer system or computer network, for performing the method, in particular method steps b) to d), according to one or more of the embodiments disclosed herein.

Preferably, referring to the computer-implemented aspects of this disclosure, in particular method steps b) to d) may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, this disclosure further discloses:

- A computer or computer network comprising at least one processor, wherein the processor is adapted to perform the method, in particular method steps b) to d), according to one of the embodiments described in this description,
- a computer loadable data structure that is adapted to perform the method, in particular method steps b) to d), according to one of the embodiments described in this description while the data structure is being executed on a computer,
- a computer program, wherein the computer program is adapted to perform the method, in particular method steps b) to d), according to one of the embodiments described in this description while the program is being executed on a computer,
- a computer program comprising program means for performing the method, in particular method steps b) to d), according to one of the embodiments described in this description while the computer program is being executed on a computer or on a computer network,
- a computer program comprising program means according to the preceding embodiment, wherein the program means are stored on a storage medium readable to a computer,
- a storage medium, wherein a data structure is stored on the storage medium and wherein the data structure is adapted to perform the method, in particular method steps b) to d), according to one of the embodiments described in this description after having been loaded into a main and/or working storage of a computer or of a computer network, and
- a computer program product having program code means, wherein the program code means can be stored or are stored on a storage medium, for performing the method, in particular method steps b) to d), according to one of the embodiments described in this description, if the program code means are executed on a computer or on a computer network.

In a further aspect of this disclosure, an analytical system for determining a concentration of at least one analyte in a fluid is disclosed.

As further used herein, the term "system" refers to an arbitrary set of interacting or interdependent component parts forming a whole. Specifically, the components may interact with each other in order to fulfill at least one common function. The at least two components may be handled independently or may be coupled or connectable. Thus, the term "analytical system" generally refers to a group of at least two elements or components which are capable of interacting in order to perform at least one analytical detection, specifically at least one analytical detection of at least one analyte of the sample. The analytical system may be an apparatus, specifically comprising at least two components.

The analytical system comprises at least one analyte sensor. The analyte sensor comprises at least two measurement electrodes, wherein at least one of the measurement electrodes comprises an analyte-responsive polymer gel. The analytical system comprises at least one signal generator device configured for generating at least one fast-transient voltage signal. The signal generator device is configured for applying the fast-transient voltage signal to the two measurement electrodes. The analytical system comprises at least one measurement unit configured for measuring at least one response signal. The analytical system comprises at least one evaluation device, wherein the evaluation device is configured for determining the analyte concentration by evaluating of the response signal.

The term "measurement unit," also denoted as measurement electronics, generally may refer to an arbitrary device, preferably an electronic device, which may be configured to detect at least one signal, in particular the response signal. The measurement unit may be configured for measuring the response signal generated in response to fast-transient voltage signal. The measurement unit may be configured for receiving the response signal and the current at the counter electrode at the same time or at at least two different time points.

The analyte sensor may be a two electrode sensor. The analyte sensor may comprise a reference resistance in series with an ionic resistivity of the analyte-responsive polymer gel.

For example, the analyte-responsive polymer gel comprises a phenylborate. The analyte-responsive polymer gel may comprise Poly(N-isopropylacryl-amide). For example, the analyte-responsive polymer gel may comprise 3-(Acrylamido)phenylboronicacid, 4-Vinylpyridine and Divinylbenzene or Acrylamide and 3-acrylamidophenylboronic acid or ethyl acrylate, 3-(Acrylamido)phenylboronic acid, N-vinylpyrrolidone and ethylene glycol dimethacrylate. Analyte-responsive polymer gels may generally comprise boronic acid groups or concanavalin A groups (Matthew J. Webber, 2015 doi:10.3109/1061186X.2015.1055749).

The analytical system may be configured for performing the method according to this disclosure. For definitions of the features of the analytical system and for optional details of the analytical system, reference may be made to one or more of the embodiments of the method as disclosed above or as disclosed in further detail below.

The method and the devices, such as the analytical system, according to this disclosure have several advantages over known electrochemical measurements. Specifically, the technique of this disclosure is easier to implement and can be realised with low-power measurement electronics. Thus, devices using the inventive method have particularly low power consumption and, therefore, may have a particularly long lifetime.

Summarizing the findings of this disclosure, the following embodiments are preferred:

Embodiment 1: A method for determining an analyte concentration in a fluid using an analyte sensor, wherein the analyte sensor comprises at least two measurement electrodes, wherein at least one of the measurement electrodes comprises an analyte-responsive polymer gel, the method comprising the following steps:

a) contacting at least the analyte-responsive polymer gel of the analyte sensor with the fluid comprising the analyte;
b) generating at least one fast-transient voltage signal and applying the fast-transient voltage signal to the measurement electrodes;
c) measuring at least one response signal;
d) determining the analyte concentration by evaluating the response signal.

Embodiment 2: The method according to embodiment 1, wherein evaluating the response signal comprises determining equivalent series resistance of the analyte sensor.

Embodiment 3: The method according to any one of embodiments 1 or 2, wherein the analyte sensor comprises a reference resistance in series with an ionic resistivity of the analyte-responsive polymer gel.

Embodiment 4: The method according to any one of embodiments 1 to 3, wherein the analyte-responsive polymer gel comprises a phenylborate.

Embodiment 5: The method according to any one of embodiments 1 to 4, wherein the analyte-responsive polymer gel comprises Poly(N-isopropylacryl-amide).

Embodiment 6: The method according to any one of embodiments 1 to 5, wherein the analyte is glucose.

Embodiment 7: The method according to any one of embodiments 1 to 6, wherein the analyte sensor is a two electrode sensor.

Embodiment 8: The method according to any one of embodiments 1 to 7, wherein the analyte sensor is placed in vivo to carry out step a).

Embodiment 9: The method according to any one of embodiments 1 to 8, wherein the fast-transient voltage signal has a square wave form or a sine wave signal form.

Embodiment 10: The method according to any one of embodiments 1 to 9, wherein the fast-transient voltage signal comprises a non-continuous signal such as a pulse, wherein a pulse duration is ≤20 μs, preferably ≤10 μs.

Embodiment 11: The method according to any one of embodiments 1 to 10, wherein the fluid is a body fluid.

Embodiment 12: A computer program comprising program means for performing the method according to any one of embodiments 1 to 11 while the computer program is being executed on a computer or on a computer network.

Embodiment 13: An analytical system for determining a concentration of at least one analyte in a fluid, wherein the analytical system comprises at least one analyte sensor, wherein the analyte sensor comprises at least two measurement electrodes, wherein at least one of the measurement electrodes comprises an analyte-responsive polymer gel, wherein the analytical system comprises at least one signal generator device configured for generating at least one fast-transient voltage signal, wherein the signal generator device is configured for applying the fast-transient voltage signal to the two measurement electrodes, wherein the analytical system comprises at least one measurement unit configured for measuring at least one response signal, wherein the analytical system comprises at least one evaluation device, wherein the evaluation device is configured for determining the analyte concentration by evaluating of the response signal.

Embodiment 14: The analytical system according to embodiment 13, wherein the analyte sensor is a two electrode sensor.

Embodiment 15: The analytical system according to any one of embodiments 13 to 14, wherein the analyte sensor comprises a reference resistance in series with an ionic resistivity of the analyte-responsive polymer gel.

Embodiment 16: The analytical system according to any one of embodiments 13 to 15, wherein the analyte-responsive polymer gel comprises a phenylborate.

Embodiment 17: The analytical system according to any one of embodiments 13 to 16, wherein the analyte-responsive polymer gel comprises Poly(N-isopropylacryl-amide).

Embodiment 18: The analytical system according to any one of embodiments 13 to 17, wherein the analytical system is configured for performing the method according to any one of embodiments 1 to 11.

Embodiment 19: The method according to any one of embodiments 13 to 18, wherein the fluid is a body fluid.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
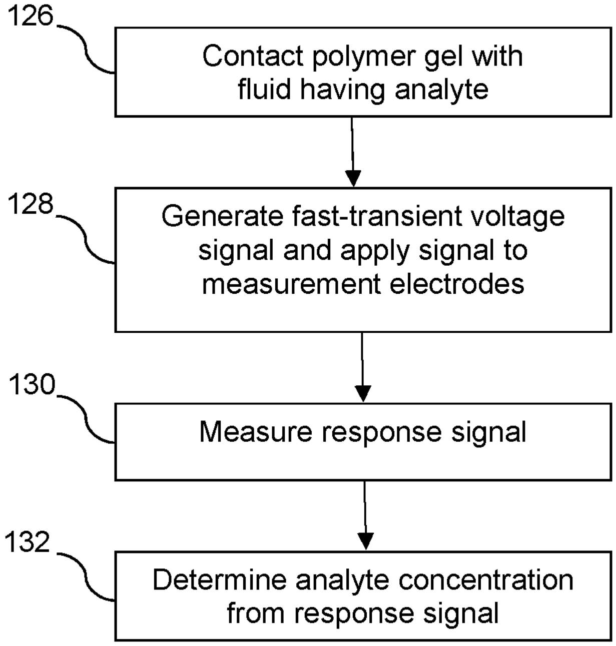
FIG. 1 shows an embodiment of a method according to this disclosure.

FIG. 1 shows an embodiment of a method for determining an analyte concentration in a fluid using an analyte sensor 110 according to this disclosure. The analyte may be an arbitrary element, component or compound which may be present in a fluid and the concentration of which may be of interest for a user. Specifically, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Specifically, the analyte may be glucose. Additionally or alternatively, however, other types of analytes may be determined and/or any combination of analytes may be determined.

The fluid may be a body fluid, may be interstitial fluid, blood, plasma, lacrimal fluid, urine, lymph, cerebrospinal fluid, bile, stool, sweat, or saliva. Generally, an arbitrary type of body fluid may be used. Preferably, the fluid is a body fluid which is present in a body tissue of a user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo.

The determining a concentration of at least one analyte may comprise a quantitative detection of the at least one analyte. As a result of the determination, at least one signal, such as at least one measurement signal, and/or at least one measurement value may be produced and/or provided which characterizes an outcome of the determination. The signal specifically may be or may comprise at least one electronic signal such as at least one voltage and/or at least one current. The at least one signal may be or may comprise at least one analogue signal and/or may be or may comprise at least one digital signal. The analyte sensor 110 may be configured for detecting quantitatively or qualitatively at least one analyte. As outlined above, the analyte sensor 110 may be used for in vivo or in vitro measurements. The analyte sensor 110 may be configured for being used for a plurality of different applications such as for monitoring an analyte in a body fluid or for monitoring at least one fermentation process. Even other applications are possible.

Figure 2:
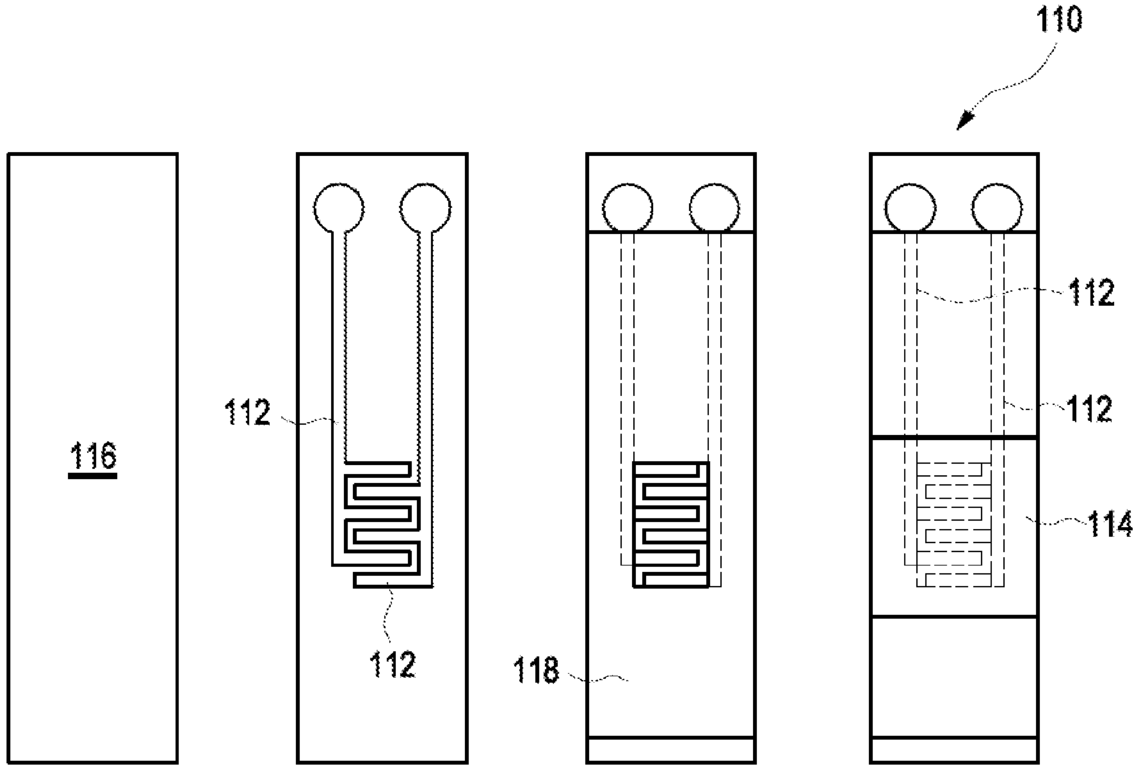
FIGS. 2A to 2D show a manufacturing process of an exemplary analyte sensor.

An embodiment of the analyte sensor 110 is shown in FIG. 2D. The analyte sensor 110 comprises at least two measurement electrodes 112. The analyte sensor 110 may be a two electrode sensor. However, embodiments are possible in which the analyte sensor 110 comprises more than two electrodes.

At least one of the measurement electrodes 112 comprises an analyte-responsive polymer gel 114. Embodiments are possible, wherein both measurement electrodes 112 comprise an analyte-responsive polymer gel 114. The analyte-responsive polymer gel 114 may be configured for changing at least one property, such as overall charge and/or volume, depending on presence of the analyte. For example, the analyte may be glucose and the analyte-responsive polymer gel 114 may be a glucose-responsive polymer gel.

For example, the analyte-responsive polymer gel 114 may comprise a phenylborate. For example, the analyte-responsive polymer gel may comprise 3-(Acrylamido)phenylboronicacid, 4-Vinylpyridine and Divinylbenzene or Acrylamide and 3-acrylamidophenylboronic acid or ethyl acrylate, 3-(Acrylamido)phenylboronic acid, N-vinylpyrrolidone and ethylene glycol dimethacrylate. Analyte-responsive polymer gels may generally comprise boronic acid groups and/or concanavalin A groups (Matthew J. Webber, 2015 doi: 10.3109/1061186X.2015.1055749).

For example, the analyte-responsive polymer 114 gel may comprise poly(N-isopropylacryl-amide). Analyte-responsive polymer gels 114 are generally known. For example, glucose-responsive polymer gels are described in "Glucose-Responsive Polymer Gel Bearing Phenylborate Derivative as a Glucose-Sensing Moiety Operating at the Physiological pH," Matsumoto et al., Biomacromolecules 2004, 5, 1038-1045. Without being bound by theory, phenylboronic acid and its derivatives are known to form reversible covalent complexes with diol units, such as with glucose. Phenylboronic acid compounds in water exist in equilibrium between the uncharged and the charged forms. Only the charged form can make a relatively stable complex with glucose through a reversible covalent bonding, whereas the complex between the uncharged form and glucose is unstable in water due to its high susceptibility to hydrolysis. Because the complex between the charged phenylborate and glucose itself is also anionically charged, the further addition of glucose induces a shift in the equilibrium to the direction of increasing the fraction of the charged forms, and vice versa. Therefore, the introduction of the phenylborate group into an amphiphilic polymer gel structure, such as that of poly(N-isopropylacryl-amide) (PNIPAAm) gel, brings about a reversible volume transition of the gel, which is mainly due to the change in the counterions' osmotic pressure synchronized with the change in the glucose concentration. The analyte-responsive polymer gel 114 may be configured for changing volume and/or charge, in particular continuously, in the presence of glucose. The change in the overall gel charge and volume may lead to the change of the analyte-responsive polymer gels' 114 ionic conductivity, which can be measured. For example, the analyte sensor 110 may be a glucose sensor comprising boronic acid based glucose-responsive polymer gel. The concentration of glucose can be determined using a fast-transient voltage signal for the measurement of the analyte sensor conductivity, which is related to the glucose concentration.

For example, in an embodiment the analyte-responsive polymer may have the following composition:

| | | |
|---|---|---|
| 3APBA | 3-(Acrylamido)phenylboronic acid | 5 mol % |
| 4VP | 4-Vinylpyridine | 93 mol % |
| DVB | Divinylbenzene | 1 mol % |
| | Irgacure 2959 | 1 mol % |

Irgacure 2959 is also known as α-Hydroxy-4-(2-hydroxyethoxy)-α-methylpropiophenon.

It is clear to the skilled person that the above-described composition of the analyte responsive polymer gel corresponds to the starting materials for the analyte responsive polymer gel. In the analyte-responsive polymer gel, the compounds are comprised in their reacted form. This is clear to the skilled person and known as such.

FIGS. 2A to 2D show a manufacturing process of an exemplary analyte sensor 110. As shown in FIG. 2A, the manufacturing of the analyte sensor 110 may comprise providing at least one isolating substrate 116. The isolating substrate 116 may comprise a convenient thickness. The isolating substrate 116 may comprise one or more of plastic, such as polyethylene terephthalate (PET), polyimide, polyvinyl chloride (PVC) or the like, ceramics, metallic substrate coated by any insulating layer, such as photoresist layer. The isolating substrate 116 may be coated by a conductive layer, for instance gold, carbon, palladium, but also any other inert conductive material, also organic conductors, like doped polythiophene. Also doped metal oxides, like ITO (indium tin oxide) or FTO (fluorine-doped tin oxide) may be used as suitable conductors. Depending on the conductive layer used, a suitable structuring method may be chosen to create the measurement electrodes 112, having preferentially an interdigitated structure, see FIG. 2B. For example, a gold layer may be used. The structuring can be done using laser ablation or chemical etching, but also any other suitable processing. Also sputtering, in particular of gold, using lift-off structuring can be used. As shown in FIG. 2C, after structuring at least one of the measurement electrodes 112 may be coated by, e.g., photoresist 118 such as to leave only the interdigitated structure exposed with well-defined surface area of the two measurement electrodes 112. Exposed portions of at least one of the measurement electrodes 112 may be coated by the analyte-responsive polymer gel 114 using, e.g., slot-die coating or simple dip-coating, see FIG. 2D.

Figure 3A:
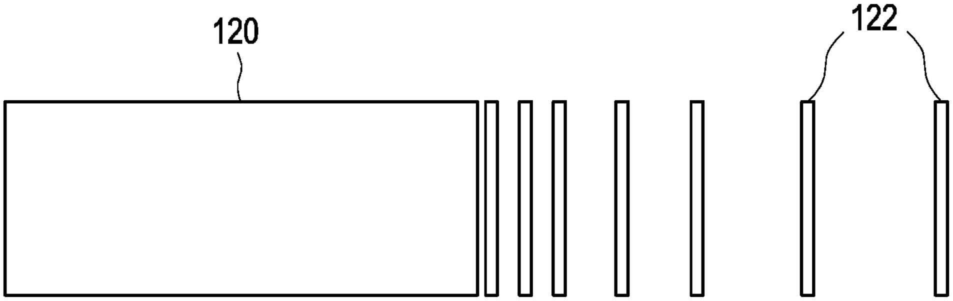
FIGS. 3A to 3C show a further manufacturing process of an exemplary analyte sensor and an embodiment of an analytical system according to this disclosure.
Figure 3B:
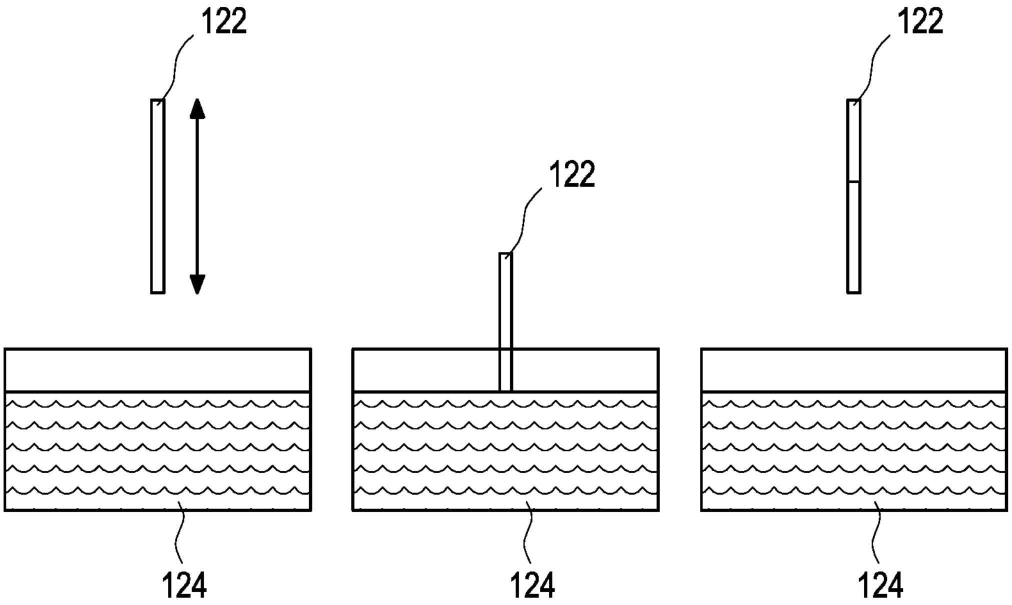

FIGS. 3A and 3B show a further manufacturing process of an exemplary analyte sensor 110. As shown in FIG. 3A, the analyte sensor 110 may be manufactured using a thin foil 120, e.g., 100 μm, double side coated with a conductive material, e.g., sputtered gold, screen-printed carbon, or anything else. The foil 120 may be cut at the way, to obtain an “I”-shaped sensor 122. One end of the I-shaped sensor 122 may be used for contacting to corresponding measurement electronics and the other end may be used as analyte sensitive portion of the analyte sensor 110 comprising the analyte-responsive polymer gel 114. In order to convert the end into an analyte sensitive portion, the analyte sensor 110 may be dip-coated in a solution of the glucose responsive polymer gel 124, see FIG. 3B. For example, a resulting layer thickness may be from 6 to 30 μm, preferentially the layer thickness may be 8 μm. Viscosity of the solution, dipping parameters, such as speed, temperature and others may be controlled at the way to obtain a glucose responsive polymer gel layer of suitable thickness. Preferentially, a non-coated portion of the conductive material is coated by an insulating layer.

Referring to FIG. 1, the method comprises the following steps:

a) (reference number 126) contacting at least the analyte-responsive polymer gel 114 of the analyte sensor 110 with the fluid comprising the analyte;
b) (reference number 128) generating at least one fast-transient voltage signal and applying the fast-transient voltage signal to the measurement electrodes 112;
c) (reference number 130) measuring at least one response signal;
d) (reference number 132) determining the analyte concentration by evaluating the response signal.

The contacting in step a) may comprise a process of exposing the at least one measurement electrode comprising the analyte-responsive polymer gel 114 to the fluid, specifically a body fluid. The analyte sensor 110 may be an in-vivo sensor. The analyte sensor 110 may be configured for being at least partially implanted into a body tissue of a user. The analyte sensor 110 may be a subcutaneous analyte sensor. The analyte sensor 110 may be configured for implantation into a body tissue of the user. More specifically the analyte sensor may be configured for continuous monitoring of the analyte. The analyte sensor 110 may be fully implantable or partially implantable. The analyte sensor 110 may be placed in vivo to carry out step a), and subsequently the further method steps.

The fast-transient voltage signal may be at least one arbitrary voltage signal, in particular an arbitrary voltage change in between the two measurement electrodes 112. The fast-transient voltage signal may have fast transient signal flanks, in particular two very steep edges. The fast-transient voltage signal may comprise a square waveform and/or a sine wave form. Specifically, the fast-transient voltage signal may comprise a fast transition square wave.

The fast-transient voltage signal may comprise a non-continuous signal such as a pulse. The pulse may have a transient change in the amplitude of the signal from a first value, also denoted baseline value, to a second value, followed by a return to the baseline value or at least approximately to the baseline value. The second value may be a higher or lower value than the baseline value. A pulse duration may be ≤50 μs, preferably ≤20 μs, more preferably ≤10 μs. The duration of the single pulse must be sufficiently long to be able to record its propagation. The fast-transient voltage signal may comprise a pulse having two edges: a leading edge or front edge, which is a first edge of the pulse and a trailing edge or back edge, which is a second edge of the pulse.

The first value may be the baseline value. The first value may be a local and/or overall minimum of the fast-transient voltage signal. The first value may be a first plateau of the fast-transient voltage signal. The first value may refer to a time point with no voltage is applied to the measurement electrodes. The second value may be a local and/or overall extremum of the fast-transient voltage signal. The second value may be a second plateau of the fast-transient voltage signal, which may be reached during application of the fast-transient voltage signal. The second value may be extremum of the fast-transient voltage signal.

The signal flank may be a rising signal flank or a falling signal flank. The signal flank of the fast-transient voltage signal may have a change in signal from the first value of the signal flank to the second value of the signal flank in a microsecond to nanosecond range. The signal flank may also be referred to as edge. The fast-transient voltage signal may have a low-to-high transition of a signal amplitude, which is equivalent to rising or positive signal flank, or high-to-low transition of a signal amplitude, which is equivalent to falling or negative signal flank. The fast-transient voltage signal may have steep edges. Specifically, the fast transition square wave may have a change in voltage from the first value to the second value below or equal 50 ns, preferably below or equal 20 ns. The change in voltage from the first value to the second value may be even faster and may be only limited by electronics such as by a fast-transient voltage generator (DAC, DO or others) or a read-out unit (voltage amplifier, ADC, or others). The faster the change of voltage (higher slew rate) and the sharper the transition to the plateau, the more precise the analyte concentration can be determined. The duration of the single fast-transient voltage signal must be sufficiently long to record the response voltage.

The fast-transient voltage signal may be applied to the measurement electrodes 112 with a known amplitude. The amplitude of the fast-transient voltage signal may vary in a broad range and must be optimized for a given set-up. Generally, the lower limit may be limited by the readout technique, which must record the response voltage, mostly by its input range and resolution and may require an additional sufficiently fast voltage amplifier.

The fast-transient voltage signal may be applied at least once to the measurement electrodes 112. The fast-transient voltage signal may be applied after a certain time after contacting the analyte sensor 110 with the fluid. The fast-transient voltage signal may be applied repeatedly to the measurement electrodes 112, in particular periodically. The fast-transient voltage signal may be applied repeatedly to the measurement electrodes 112, in particular in time intervals from minutes to seconds. A measurement frequency may depend on how often measurement values are required. The method may further comprise determining a combined measurement value for reducing a measurement uncertainty. The determining of a combined measurement value may comprise determining of one or more of an average value, a mean value, a median, using a more complex filter such as a Kalman filter. For example, measurement values may be obtained every second and the 60 measurement results may be averaged to a minute-value. The measurement frequency may depend on the application of the analyte sensor. For monitoring of analyte in a body fluid the frequency may be short, whereas for monitoring a fermentation process such as in wine or beer the measurement frequency may be less frequent.

Figure 3C:
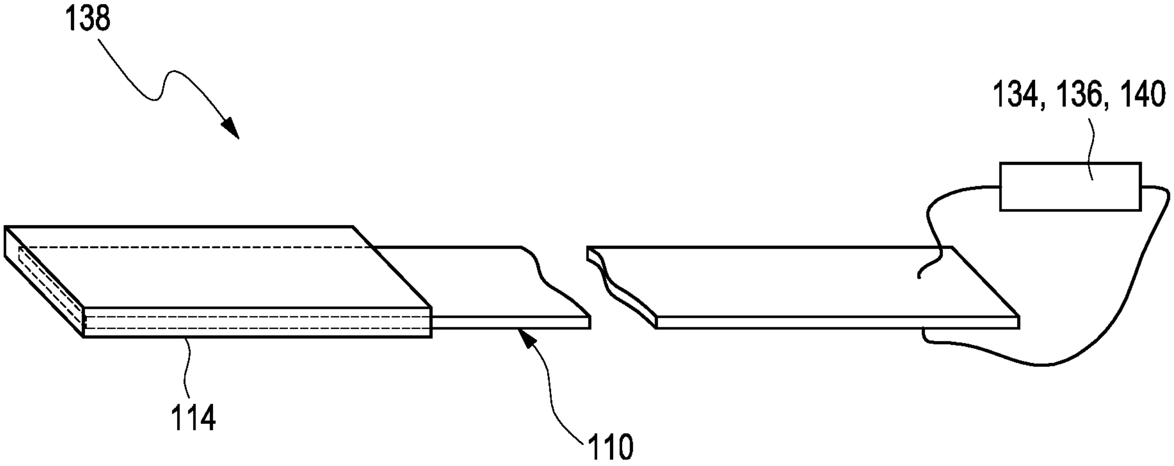

The fast-transient voltage signal may be generated by at least one signal generator device 134, shown in FIG. 3C. The signal generator device 134 may be configured to generate a voltage signal. The signal generator device 134 may comprise at least one voltage source. The signal generator device 134 may comprise at least one function generator selected from the group consisting of: at least one square wave generator and at least one sine wave generator. The signal generator device 134 may also generate a single pulse which may be unsymmetrically. The signal generator device 134 may be part of measurement electronics of the analyte sensor 110 and/or may be connected to the analyte sensor and may be designed as a separate device. The signal generator device 134 may be configured for applying the fast-transient voltage signal to the measurement electrodes 112.

Figure 4A:
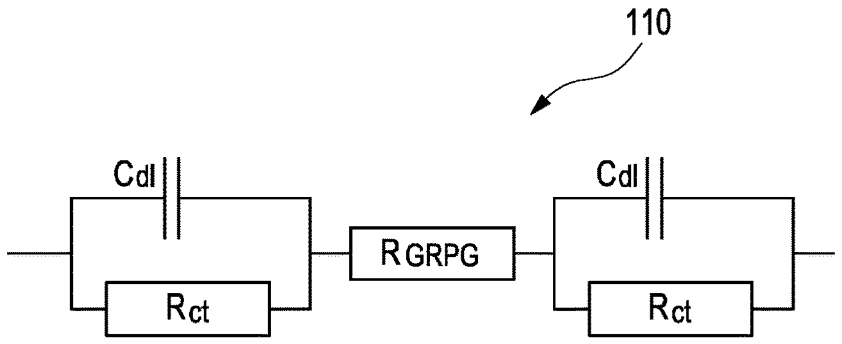
FIGS. 4A and 4B show equivalent circuit of an analyte sensor.
Figure 4B:
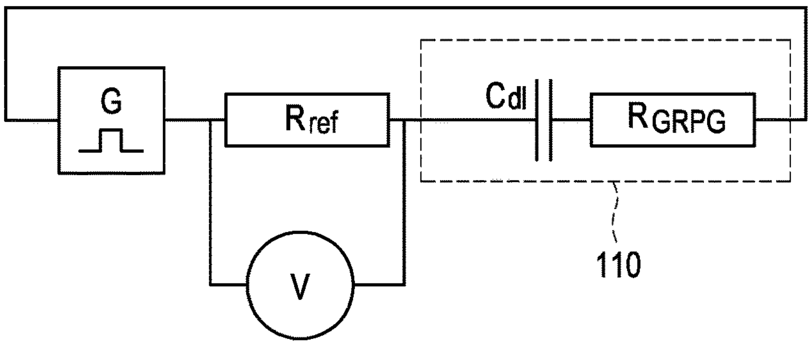

FIGS. 4A and 4B show equivalent circuit of the analyte sensor 110. Each measurement electrode 112 of the analyte sensor 110 may have a capacity caused by a formed electrochemical double layer, denoted $C_{dl}$. Ionic resistivity of the analyte-responsive polymer gel 114, specifically a layer of polymer gel, between the two measurement electrodes 112 may be represented as $R_{GRPC}$. Moreover, charge transfer resistances Re may be present at electrode-electrolyte interfaces. At the rest there is no potential applied between the both measurement electrodes 112 and surfaces of the measurement electrodes 112 may be inert. In particular, there is no electron transfer between the electrodes and electrolyte and the Ret is, therefore, infinitely large. The two $C_{dl}$ may be connected serially and are thus not differentiable. Thus, as shown in FIG. 4B, the whole analyte sensor 110 can be represented as a single $C_{dl}$ serially connected with $R_{GRPC}$. The signal generator device 134 may be configured for keeping the potential difference between the two measurement electrodes 112 at zero in the rest.

The response signal may be a measured propagation of the applied fast-transient voltage signal. The response signal may be a change of the applied fast-transient voltage signal. The response signal may directly or indirectly refer to equivalent series resistance of the analyte sensor 110. The response signal may be the ohmic and capacitive characterization of the analyte sensor 110 in its in-vivo surroundings.

Figure 5:
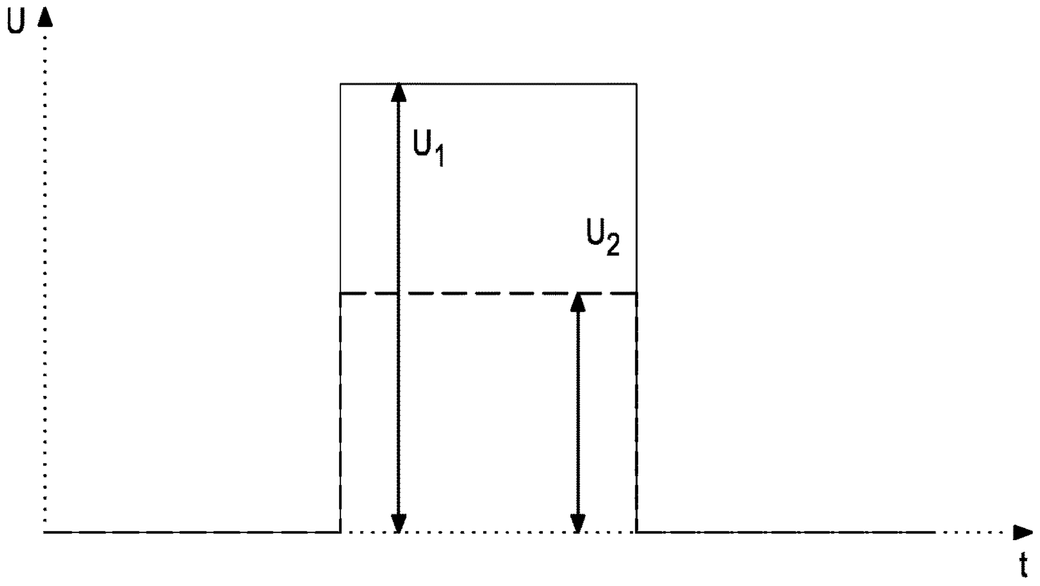
FIG. 5 shows graphical representation of a fast-transient signal and response signal.

As shown in FIG. 4B, the response voltage may be measured at a reference resistance, denoted $R_{ref}$. The analyte sensor 110 may comprise at least one reference resistance in series with an ionic resistivity of the analyte-responsive polymer gel 114. The reference resistance may be selected suitable for determining a value to be measured such as the electrical resistance of the ionic resistivity of the analyte-responsive polymer gel $R_{GRPC}$. A value of the reference resistance $R_{ref}$ may be preferentially in the range of the $R_{GRPC}$. The reference resistance may be an average value determined, specifically pre-determined, from a plurality of reference measurements. The reference resistance must reflect the measurement range of the analyte-responsive polymer gel 114. The reference resistance may reflect required measurement tolerances. During determination of the $R_{GRPC}$ determination, the signal generator device 134, denoted “G” in FIG. 4B, may apply the fast-transient voltage signal with known amplitude $U_1$ to the measurement electrodes 112. Simultaneously a voltage drop $U_2$ may be measured at the reference resistance $R_{ref}$. FIG. 5 shows a graphical representation of an exemplary fast-transient signal with known amplitude $U_1$ and response signal measured as voltage drop $U_2$ as a function of time t.

Evaluating the response signal may comprises determining the equivalent series resistance of the analyte sensor 110. Knowing the amplitude of the applied voltage and the amplitude measured at the $R_{ref}$, as well as the value of the $R_{ref}$, $R_{GRPC}$ can be calculated as:

$$R_{GRPC} = R_{ref}\frac{U_2}{(U_1 - U_2)}$$

The evaluation of the response signal may be performed by at least one evaluation device 136. The evaluation device 136 may be configured to derive the equivalent series resistance. As an example, the evaluation device 136 may be or may comprise one or more integrated circuits, such as one or more application-specific integrated circuits (ASICs), and/or one or more data processing devices, such as one or more computers, preferably one or more microcomputers and/or microcontrollers. Additional components may be comprised, such as one or more preprocessing devices and/or data acquisition devices, such as one or more devices for receiving and/or preprocessing of the response signal, such as one or more converters and/or one or more filters. The evaluation device 136 may comprise one or more data storage devices. The evaluation device 136 may comprise one or more interfaces, such as one or more wireless interfaces and/or one or more wire-bound interfaces. The evaluation device 136 may comprise a microprocessor, a cellular phone, a smart phone, a personal digital assistant, a personal computer, or a computer server.

The evaluation may further comprise determining the concentration of the analyte from the equivalent series resistance by using at least one pre-determined relationship. For example, the pre-determined relationship may be a linear relationship. For example, the pre-determined relationship may be stored in at least one database of the evaluation device 136.

FIG. 3C shows further an embodiment of an analytical system 138 according to this disclosure. The analytical system 138 comprises the analyte sensor 110. The analytical system 138 comprises the signal generator device 134 configured for generating at least one fast-transient voltage signal. The signal generator device 134 is configured for applying the fast-transient voltage signal to the two measurement electrodes 112. The analytical system 138 comprises at least one measurement unit 140, also denoted as measurement electronics, configured for measuring at least one response signal. The analytical system 138 comprises the evaluation device 136, wherein the evaluation device 136 is configured for determining the analyte concentration by evaluating of the response signal.

Figure 6A:
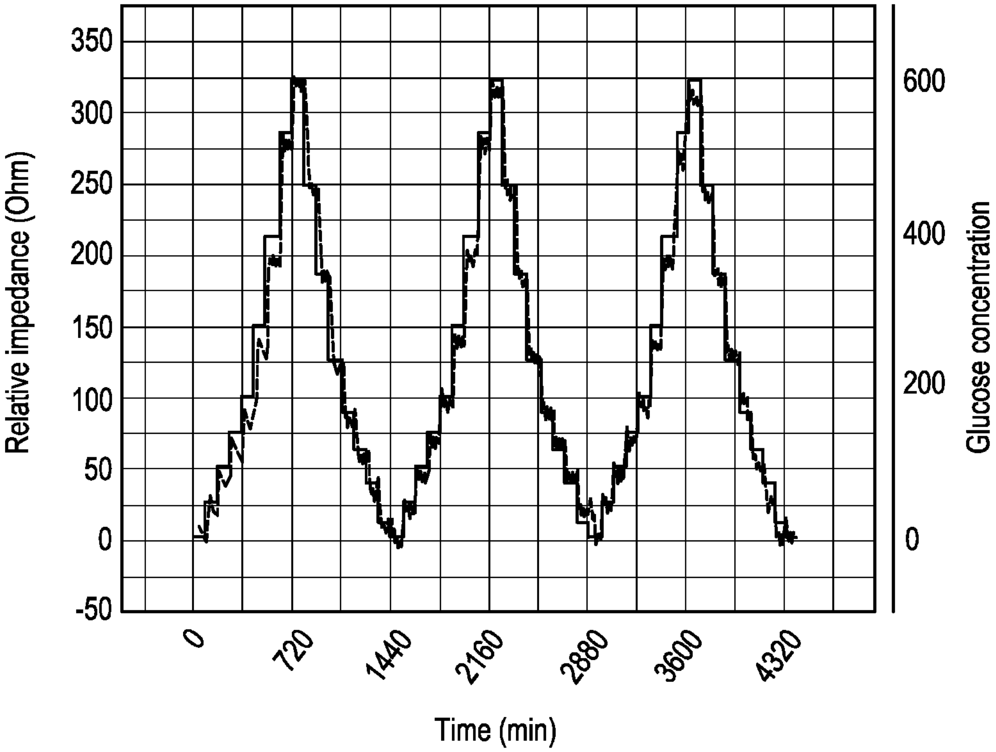
FIGS. 6A and 6B show experimental results.
Figure 6B:
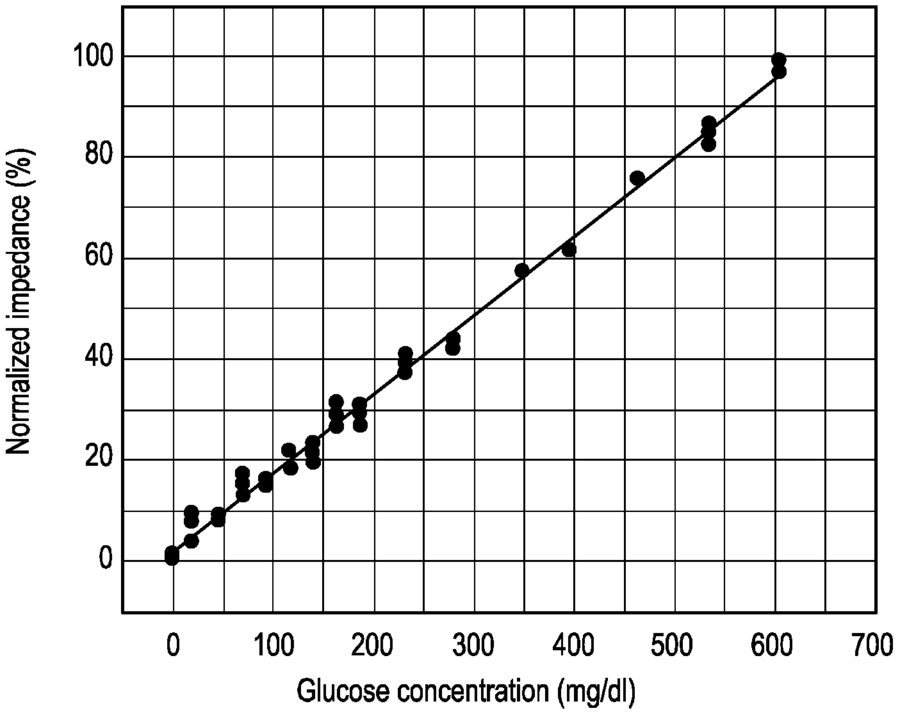

FIGS. 6A and 6B show experimental results. For the experimental setup, the following sensor design was used: A double sided gold coated polyimide substrate having one open gold surface at each side. The active surface area on the one side was 1.6 $mm^2$, and on the other side 0.36 $mm^2$. The substrate was coated by glucose responsive polymer gel 124 by means of dip coating in the reactive mixture of monomer and crosslinker. The resulting dry glucose responsive polymer gel 124 layer thickness was 8 μm. The experimental set-up comprises a flow cell constantly kept at 37±0.1° C. The mixing unit of the setup is able to mix a pure 100 mM PBS with 100 mM PBS containing 600 mg/dl glucose in variable ratios. The resulting PBS electrolyte may comprise 0-600 mg/dl glucose. The analyte sensor 110 is fixed in the flow cell, such as its sensitive part is constantly surrounded by the tempered electrolyte with the defined glucose concentration. The measurement procedure was as follows: The analyte sensor 110 was placed in the flow cell and connected to the electronics. The electronics generated one measurement value per minute. The analyte sensor 110 was preconditioned in the pure PBS for few hours until its base impedance value was stable. For the given sensor the base impedance (at zero glucose) was 4.4 kOhm. The glucose concentration profile (solid line) comprised steps from 0 to 600 mg/dl and the duration of each step was 90 minutes. The measurement was running for three days and the resulted curve (dashed line) after subtraction of the base impedance is depicted in FIG. 6A.

FIG. 6B depicts normalized impedance vs. absolute glucose values recorded over the three days. The resulted slope shows the percentual change in the impedance with the glucose concentration and amounted to 0.156%/mg/dl, while the R-Square amounted to 0.995, which indicates a very good linearity of the analyte sensor 110 in this wide range of glucose concentrations.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS

110 analyte sensor
112 measurement electrode
114 analyte-responsive polymer gel
116 isolating substrate
118 photoresist
120 foil
122 I-shaped sensor
124 glucose responsive polymer gel
126 contacting
128 generating
130 measuring
132 determining the analyte concentration
134 signal generator device
136 evaluation device
138 analytical system
140 measurement unit

What is claimed is:

1. A method for determining an analyte concentration in a fluid using an analyte sensor having at least two measurement electrodes, one of the measurement electrodes having an analyte-responsive polymer gel, the method comprising:
a) contacting at least the analyte-responsive polymer gel with the fluid having the analyte;
b) generating a non-continuous fast-transient voltage signal and applying the non-continuous fast-transient voltage signal to the measurement electrodes, wherein the fast-transient voltage signal comprises a pulse having a pulse duration selected from the group consisting of ≤20 μs and ≤10 μs;
c) measuring a response signal, wherein the response signal is a measured propagation of the applied fast-transient voltage signal; and
d) evaluating the response signal to determine the analyte concentration.

2. The method according to claim 1, wherein evaluating the response signal comprises determining equivalent series resistance of the analyte sensor.

3. The method according to claim 1, wherein the analyte sensor comprises a reference resistance in series with an ionic resistivity of the analyte-responsive polymer gel.

4. The method according to claim 1, wherein the analyte-responsive polymer gel comprises a phenylborate.

5. The method according to claim 1, wherein the analyte-responsive polymer gel comprises Poly(N-isopropylacrylamide).

6. The method according to claim 1, wherein the analyte is glucose.

7. The method according to claim 1, wherein the analyte sensor is a two electrode sensor.

8. The method according to claim 1, wherein the analyte sensor is placed in vivo to carry out step a).

9. The method according to claim 1, wherein the fast-transient voltage signal has a square waveform or a sine wave signal form.

10. A non-transitory computer readable medium having stored thereon computer executable instructions for performing the method according to claim 1.

11. An analytical system for determining an analyte concentration in a fluid, the system comprising:
an analyte sensor having at least two measurement electrodes, one of the measurement electrodes having an analyte-responsive polymer gel;
a signal generator configured for generating a non-continuous fast-transient voltage signal and applying the non-continuous fast-transient voltage signal to the measurement electrodes, wherein the fast-transient voltage signal comprises a pulse having a pulse duration selected from the group consisting of ≤20 μs and ≤10 μs;

a measurement unit configured for measuring a response signal, wherein the response signal is a measured propagation of the applied fast-transient voltage signal; and an evaluator configured to evaluate the response signal to determine the analyte concentration.

12. The analytical system according to claim 11, wherein the analyte sensor comprises a reference resistance in series with an ionic resistivity of the analyte-responsive polymer gel.

13. The analytical system according to claim 11, wherein the analyte-responsive polymer gel comprises a phenylborate and/or Poly(N-isopropylacryl-amide).

* * * * *